US006312441B1

(12) United States Patent
Deng

(10) Patent No.: US 6,312,441 B1
(45) Date of Patent: Nov. 6, 2001

(54) POWERED HANDPIECE FOR PERFORMING ENDOSCOPIC SURGICAL PROCEDURES

(75) Inventor: Wenjie Deng, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/262,466

(22) Filed: Mar. 4, 1999

(51) Int. Cl.⁷ .................................................. A61B 17/32
(52) U.S. Cl. ......................................................... 606/170
(58) Field of Search ..................................... 606/167, 168, 606/169, 170, 180; 30/93, 97; 604/30, 32

(56) References Cited

U.S. PATENT DOCUMENTS

| | | | |
|---|---|---|---|
| 4,173,328 | * 11/1979 | Karbo | 604/32 |
| 4,447,177 | * 5/1984 | Ochiai et al. | 408/161 |
| 4,451,185 | * 5/1984 | Yamakage | 408/2 |
| 4,925,450 | * 5/1990 | Imonti et al. | 604/32 |
| 5,203,769 | * 4/1993 | Clement et al. | 604/32 |
| 5,241,990 | * 9/1993 | Cook | 604/32 |
| 5,492,527 | * 2/1996 | Glowa et al. | 606/170 |
| 5,685,796 | * 11/1997 | Chen et al. | 475/320 |
| 5,693,062 | * 12/1997 | Stegmann et al. | 606/170 |
| 5,712,543 | * 1/1998 | Sjostrom | 606/170 |
| 5,733,298 | * 3/1998 | Berman et al. | 606/170 |
| 5,792,157 | * 8/1998 | Mische et al. | 606/170 |
| 5,792,167 | 8/1998 | Kablik et al. . | |
| 5,871,493 | * 2/1999 | Sjostrom et al. | 606/170 |
| 5,888,200 | * 3/1999 | Walen | 606/170 |
| 5,910,152 | * 6/1999 | Bays | 606/170 |
| 5,975,218 | * 11/1999 | Liau | 173/216 |
| 5,993,454 | * 11/1999 | Longo | 606/80 |
| 6,010,477 | * 1/2000 | Bays | 606/170 |

OTHER PUBLICATIONS

Stryker Endoscopy Hummer II, Handpiece Assembly Documents, Sep., 1997.*
Stryker® Hummer II™ Handpiece Assembly Documents, Sep., 1997, 13 sheets.

* cited by examiner

Primary Examiner—Henry J. Recla
Assistant Examiner—Tan-Uyen T. Ho
(74) Attorney, Agent, or Firm—Flynn, Thiel, Boutell & Tanis, P.C.

(57) ABSTRACT

A powered surgical handpiece (20) designed to actuate cutting accessories (22) such as those used to perform endoscopic surgery. The handpiece includes a housing (24) that contains a motor (26). The motor is within its own housing (46). A motor rotor (88) extends out of the motor housing (46) and engages a gear reduction assembly (76). The gear reduction assembly includes a planetary gear assembly for which the motor rotor (88) is the sun gear. The motor housing (46) is formed to have integral therewith a ring gear (96) that is located around the portion of the motor rotor that extends out of the motor housing. There is a valve (44) for regulating suction flow through the handpiece. The valve sits in a valve bore (110) that is closed at one end. There is also coupling assembly (28) for releasably holding the cutting accessory to the housing so that the cutting accessory engages with the gear assembly. The components forming the coupling assembly are disassembled from each other to facilitate maintenance of the handpiece.

29 Claims, 8 Drawing Sheets

POWERED HANDPIECE FOR PERFORMING ENDOSCOPIC SURGICAL PROCEDURES

FIELD OF THE INVENTION

This invention is related generally to a powered handpiece useful for performing endoscopic surgical procedures and, more particularly, to a handpiece that is economic to assemble, reliable and easy to maintain.

BACKGROUND OF THE INVENTION

Endoscopic surgical procedures are routinely performed in order to accomplish various surgical tasks. In an endoscopic surgical procedure, small incisions, called portals, are made into the patient. An endoscope, which is a device that allows medical personnel to view the surgical site, in inserted in one of the portals. Surgical instruments used to perform a specific surgical task are inserted into other of the portals. The surgeon views the surgical site through the endoscope to determine how to manipulate the surgical instruments in order to accomplish the surgical procedure. An advantage of performing endoscopic surgery is that since the portions of the body that are cut open are minimized, the portions of the body that need to heal after surgery are likewise reduced. Moreover, during an endoscopic surgical procedure, only a relatively small portions of the patient's internal organs and tissue are exposed to the open environment. This minimal opening of the patient's body lessens the extent to which a patient's organs and tissue are open to infection.

The ability to perform endoscopic surgery has been enhanced by the development of powered surgical tools especially designed to perform endoscopic surgical procedures. One such tool, for example, is sold by the Applicant's Assignee under the trademark HUMMER II. This tool is in form of a cylindrical handpiece designed to be held in the hand of the surgeon. Internal to the handpiece there is a motor. A front end of the handpiece is provided with a coupling assembly for releasably holding a cutting accessory. The types of cutting accessories that are attached to these handpiece include edgers, resectors, planers and burrs. Integral with the motor and coupling assembly is a means for transmitting the rotary power developed by the motor to the cutting accessory.

The handpiece also has a suction conduit. This is because, in an endoscopic surgical procedure, irrigating fluid is introduced into the surgical site. This fluid serves as a transport media for removing tissue and debris from the surgical site. In order to remove the irrigating fluid, and the material in the fluid, a suction path is provided through the cutting accessory and the handpiece. A suction pump is connected to the handpiece and provides the suction force for drawing the fluid and material away from the surgical site. In order to control the suction flow through the cutting accessory and the handpiece, the handpiece is provided with a manually operated valve. Thus, with a single handpiece, a surgeon both manipulates the cutting accessory and control the suction of material away from the surgical site.

While current powered surgical handpiece have proven to be useful tools, they are expensive to manufacture and can be difficult to maintain. This is because the handpiece, which is typically less than 14 cm long and less than 3 cm in diameter, must contain the motor, the coupling assembly, the suction conduit and the valve for controlling fluid flow through the suction conduit. Each of these subassemblies has a number of components that must cooperate with the complementary components of the handpiece. For example, the motor is often provided with a speed reducing/torque increasing planetary gear assembly. This assembly includes a fixed ring gear. Given the relatively small size of this ring gear, and the forces to which it is subjected, the gear is typically manufactured from stainless steel. Thus, this gear is provided as a stand-alone component internal to the handpiece.

Also, many handpieces are provided with lever-set suction valves for regulating fluid flow through the suction conduit. This type of valve includes a valve body that is rotatably fitted in the handpiece. Bosses extend outwardly from the opposed ends of the valve body through the handpiece. The bosses are connected to exposed levers on the handpiece that a surgeon pivots to set the valve. An advantage of this arrangement is that once assembled, the valve is essentially a single moving part. However, this assembly is formed out of numerous components.

Moreover, the coupling assemblies of many powered endoscopic surgical handpieces are likewise formed out of numerous components. This is because these assemblies typically must be designed to hold the rotating member of the cutting accessory to a complementary element integral with the gear train, hold a static outer shell of the cutting accessory in place, and provide a seal around the rotating member in order to ensure that there will be good suction flow through the rotating member. Currently, some of these coupling assemblies are constructed so that, once assembled, they are difficult, if not impossible, to disassemble. The difficulty associated with disassembling these coupling assemblies makes it difficult to perform maintenance on the handpieces with which they are associated.

Thus, collectively, having to provide the numerous components of the current endoscopic handpieces and that fact that some of their components cannot be readily disassembled makes it relatively expensive to both provide and maintain these handpieces.

SUMMARY OF THE INVENTION

This invention relates generally to a new powered surgical handpiece designed to perform endoscopic surgical procedures that is relatively economical to assemble and to maintain. More specifically, this handpiece includes a suction valve and a motor/gear assembly that both have few components and an easy to assemble coupling assembly. The suction valve, the motor/gear assembly and the coupling assembly of this invention are also relatively easy to disassemble.

BRIEF DESCRIPTION OF THE DRAWINGS

The invention is pointed out with particularity in the claims. The above and further advantages may be better understood by reference to the following description taken in conjunction with the accompanying drawings, in which:

DETAILED DESCRIPTION

Figure 1:
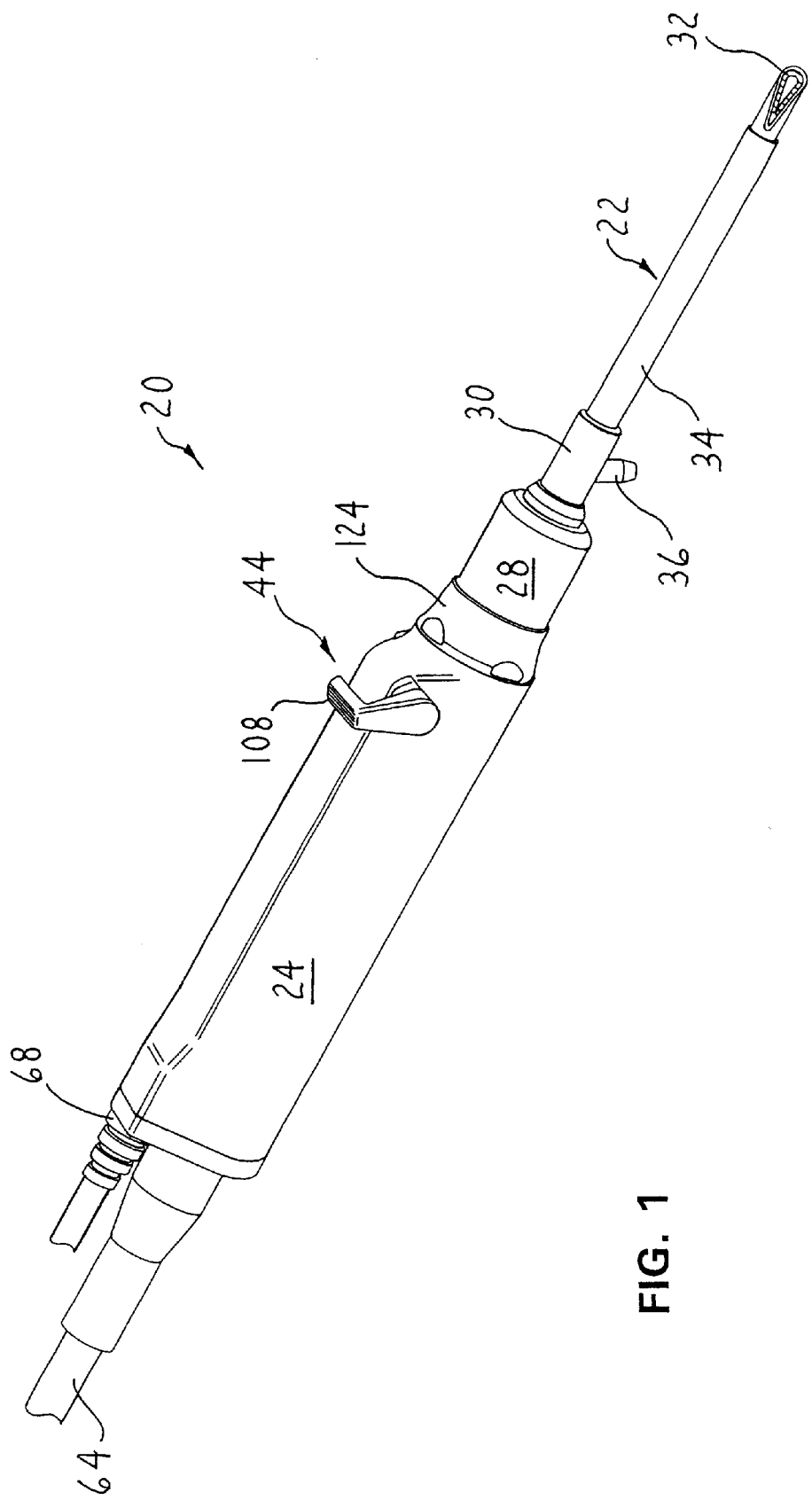
FIG. 1 is a perspective view of an endoscopic surgical handpiece of this invention that depicts a complementary cutting accessory secured to the handpiece.
Figure 2:
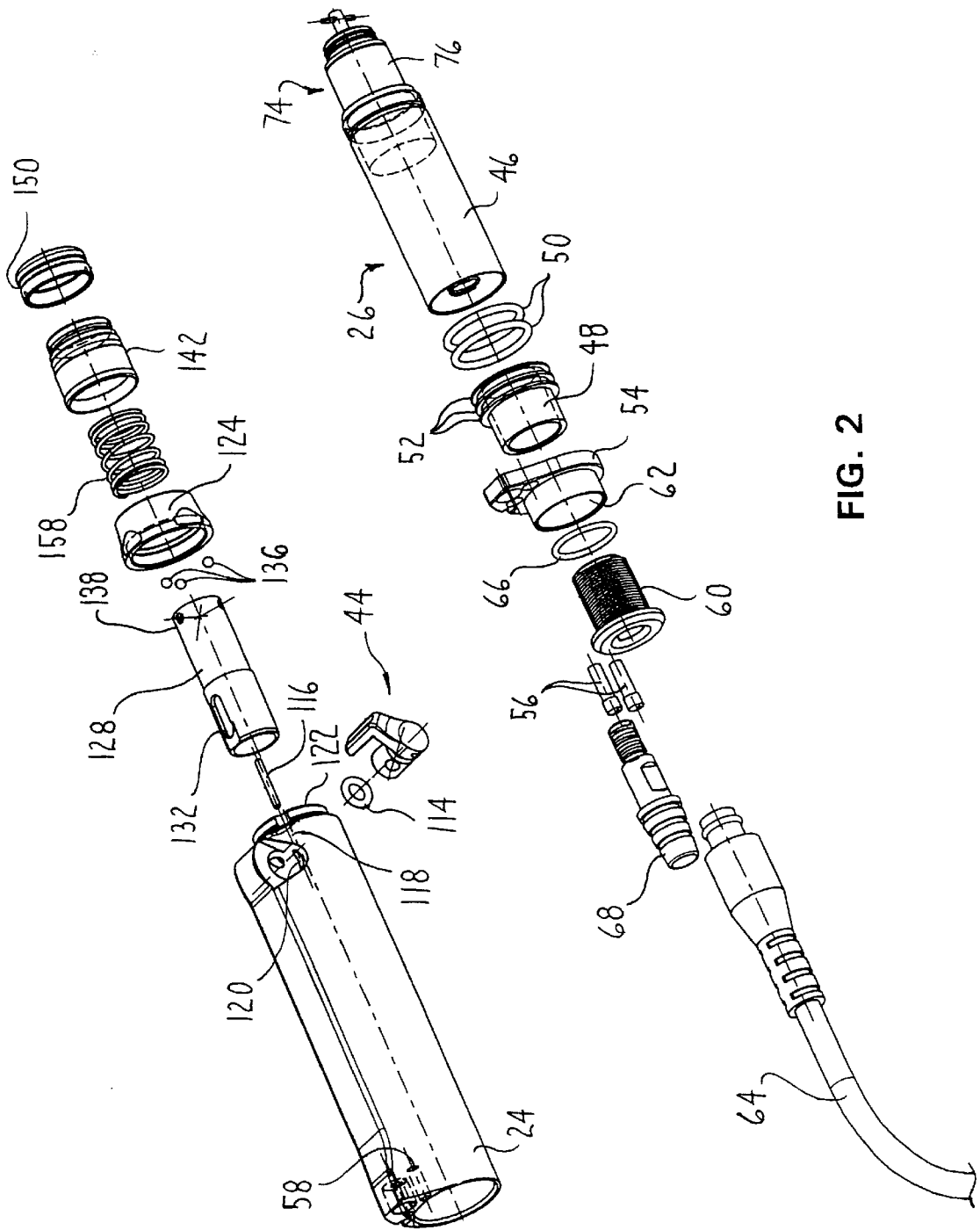
FIG. 2 an exploded view of the components forming the handpiece.

FIGS. 1 and 2 depict an endoscopic handpiece 20 of this invention and a complementary cutting accessory 22 attached to the handpiece. The handpiece 20 includes a generally cylindrical housing 24 that is open at both ends. A motor 26 is disposed inside the housing 24. A coupling assembly 28 is mounted to the front end of the housing 24 for removably holding the cutting accessory 22 to the handpiece.

The cutting accessory 22 includes an a rotating hub (not illustrated) that engages the drive pin 79 of an output shaft 78 (FIG. 4) which is connected to the motor 26 as described hereinafter. The cutting accessory 22 includes a static outer hub 30 that surrounds the rotating hub that is held static by the coupling assembly 28. A rotating cutting element, such as a planer 32, extends forward from and rotates in unison with the rotating hub. An outer shell 34 extends forward from the outer hub 30 and surrounds the elongated shaft of the planer 32. Irrigating fluid is introduced into the annular space between the inner wall of the outer shell 34 and the shaft of the planer 32 through an irrigation port 36 in an exposed section of the outer hub 30. The shaft of the planer 32 is open around its cutting surfaces. A suction is drawn through the handpiece 20 and shaft of the planer 32 to remove irrigating fluid and the material entrained in the irrigating fluid. A more detailed discussion of the construction of the cutting accessory 22 is found in the Applicant's Assignee's U.S. Pat. No. 5,792,167, entitled SURGICAL IRRIGATION PUMP AND TOOL SYSTEM, issued Aug. 11, 1998, which is incorporated herein by reference.

Figure 3:
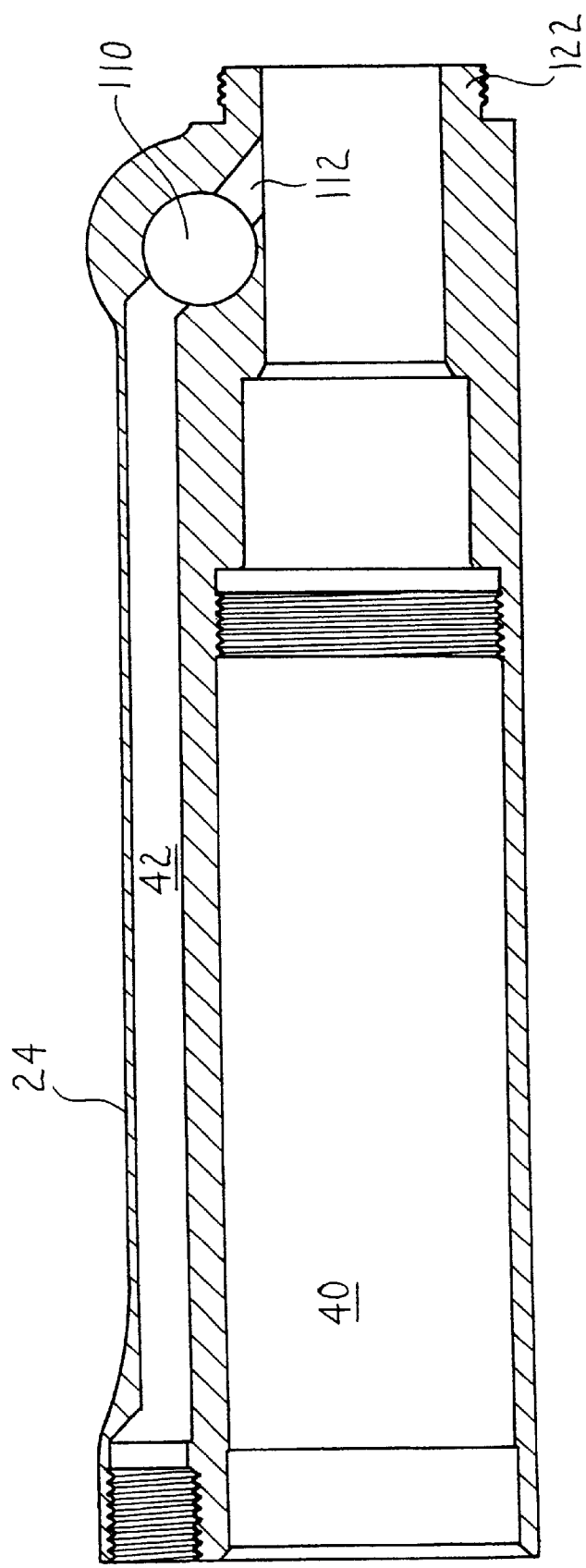
FIG. 3 is a cross sectional view of the housing of the handpiece.

As seen by reference to FIGS. 2 and 3, the handpiece housing 24 has a first, large diameter main bore 40 which is approximately 1.9 to 2.2 cm in diameter. The motor 26 is housed and the coupling assembly 28 is partially mounted in the main bore 40. Extending parallel with and located above main bore 40, handpiece housing 24 is formed to have a suction bore 42 that has a diameter of approximately 0.25 to 0.40 cm. A suction is drawn through suction bore 42. As will be described hereinafter, this is the suction force that is applied through the cutting accessory 22 to draw irrigating fluid and debris away from the surgical site. Fluid flow through suction bore 42 is regulated by a valve 44 located in the front end of the handpiece housing 24. (In this application "front", "forward" and "distal" shall be understood to mean towards the cutting accessory 22).

As seen by FIG. 2, motor 26 is encased in a cylindrical motor housing 46 that is statically fitted in the main bore 40 of handpiece housing 24. A seal retainer 48 is disposed behind the motor housing 46 in the main bore 40. Two O-rings 50 are held between flat, annular flanges 52 integrally formed by the seal retainer 48. The O-rings 50 provide a liquid tight barrier to prevent water vapor from penetrating towards the motor 26. A plate-like connector housing 54 is disposed over the open rear end of handpiece housing 24. Two screws 56, which extend through openings in the connector housing 54, (opening not identified) and engage into threaded bores 58 (depicted in phantom) in the rear of the handpiece housing 24 hold the connector housing 54 to the handpiece housing 24.

A plug-like electrical connector 60 is threadedly secured into a complementary threaded bore 62 formed in the connector housing 54. Electrical connector 60 provides the socket to which an external power cable 64 is removably attached to the handpiece 20. Wires, (not illustrated), conduct the energization current from the cable 64 to the motor 26. An O-ring 66 is fitted around the exposed, large diameter head of connector 60 and the reduced diameter threaded section. O-ring 66 provides a vapor barrier between the outside environment and the inside of the handpiece housing 24.

Figure 7:
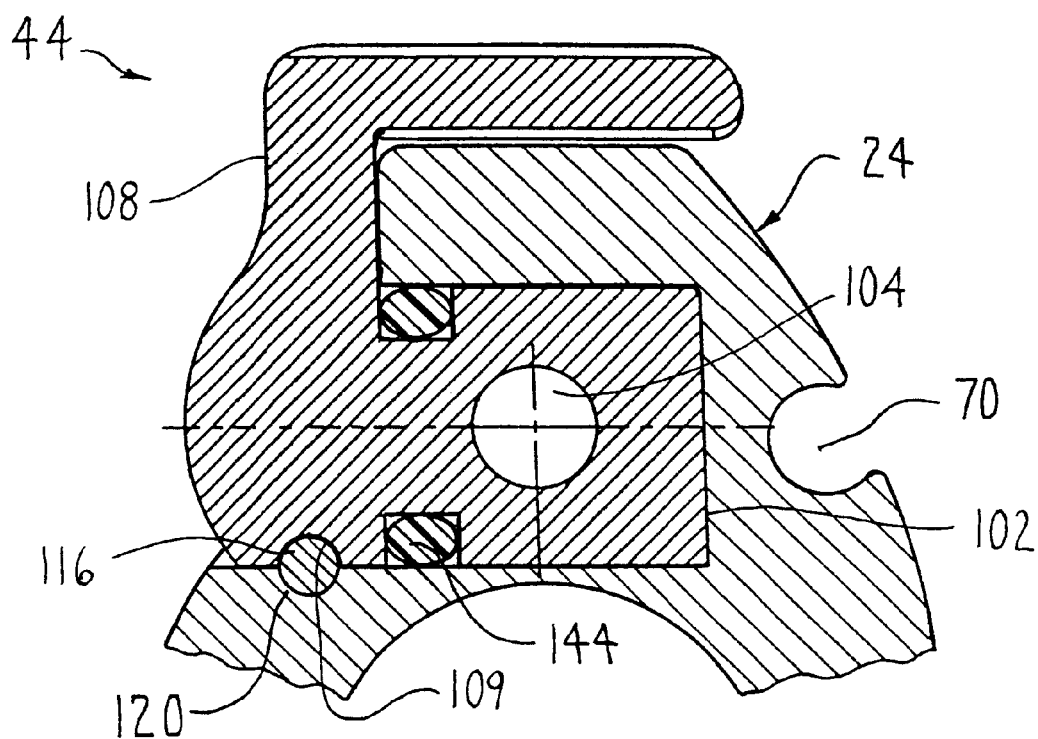
FIG. 7 is a cross sectional view depicting how the suction valve is mounted to the handpiece housing.

A suction fitting 68 extends through an opening in the connector housing 54 and into the suction bore 42 of handpiece housing 20. Complementary threading on the outer surface of fitting 68 and around the inside of the rear end of the suction bore hold the fitting to the handpiece housing 24. It will be further noted from FIG. 7 that the outer surface of the handpiece housing 24 is formed with an elongated groove 70. A removable irrigation line (not illustrated) is seated in groove. This irrigation line serves as the conduit through which irrigating fluid is flowed to the irrigation port 36 of the cutting accessory 22.

Figure 4:
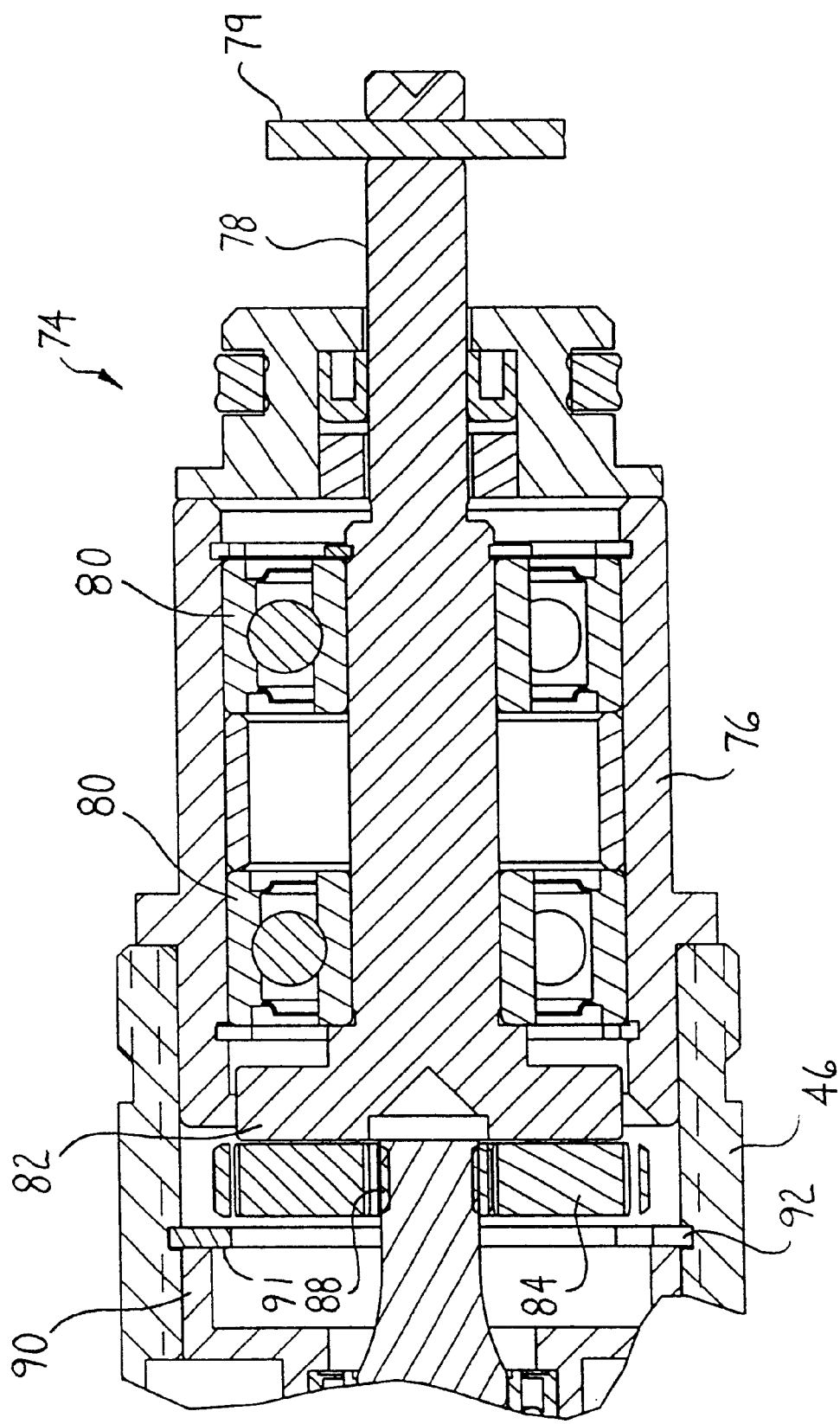
FIG. 4 is a cross sectional view depicting how the motor and gear assembly are fitted together.
Figure 6:
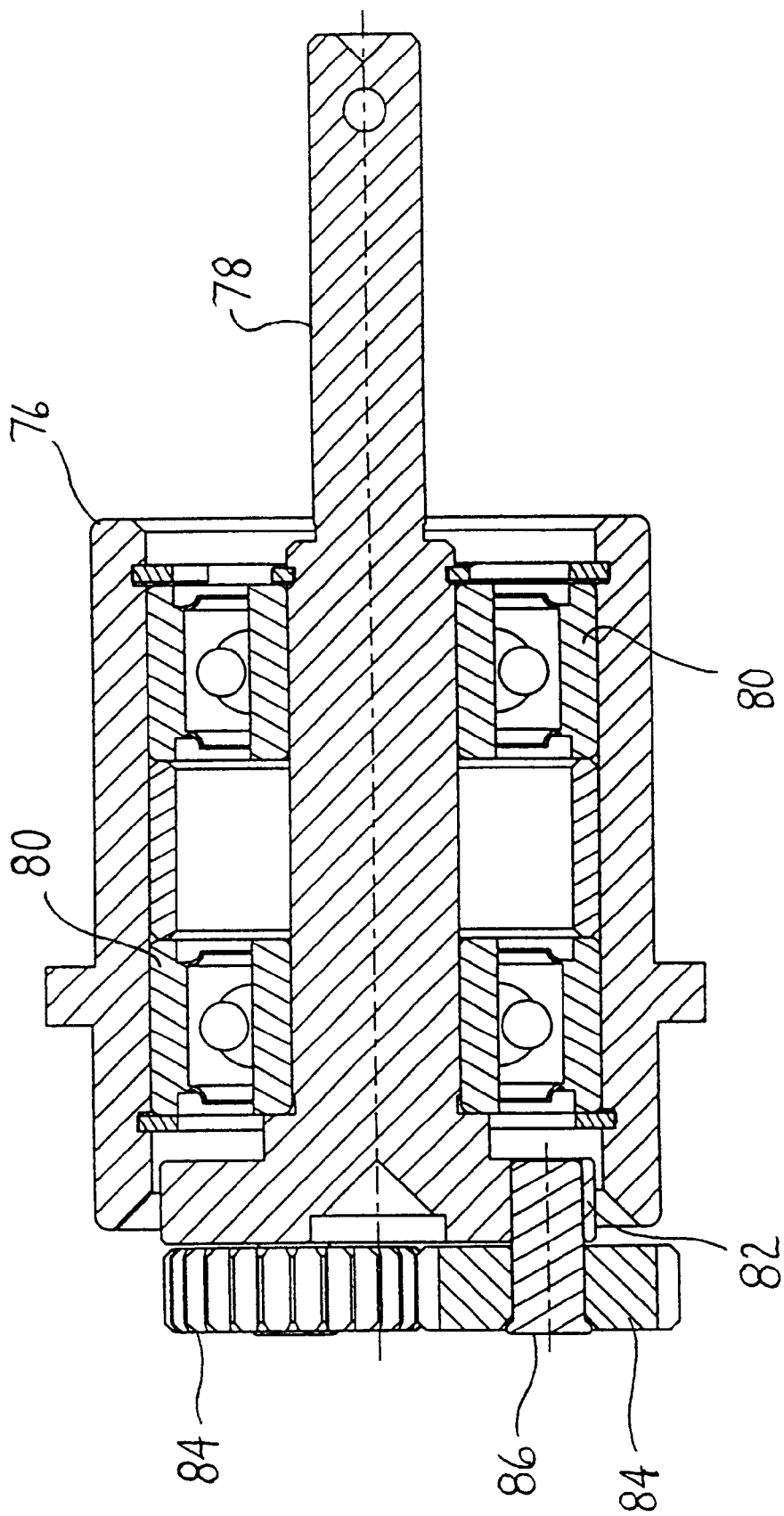
FIG. 6 is a cross sectional view of the gear assembly.
Figure 8:
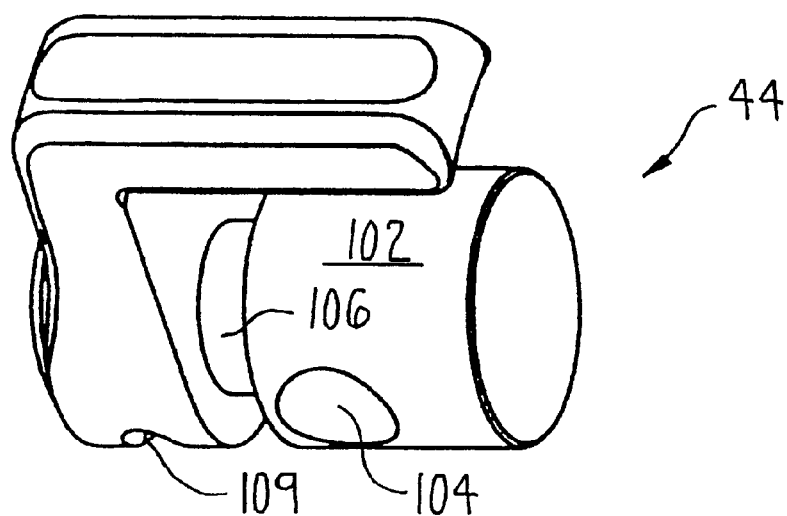
FIG. 8 is a perspective of the suction valve.

As can be seen from FIGS. 2, 4 and 6, the motor 26 is coupled directly a gear assembly 74. Gear assembly 74 reduces the speed, increases the torque, of the rotational force produced by the motor 26. Gear assembly 74 includes a gear housing 76 which is fitted over the front end of motor housing 46. Output shaft 78 extends through gear housing 76. The output shaft 78 is rotatably fitted in gear housing 76 by bearing assemblies 80. The rear end of output shaft 78 is formed with a ring-shaped carrier plate 82. Planet gears 84 are rotatably mounted to fixed axles 86 that extend rearwardly from carrier plate 82.

Figure 5:
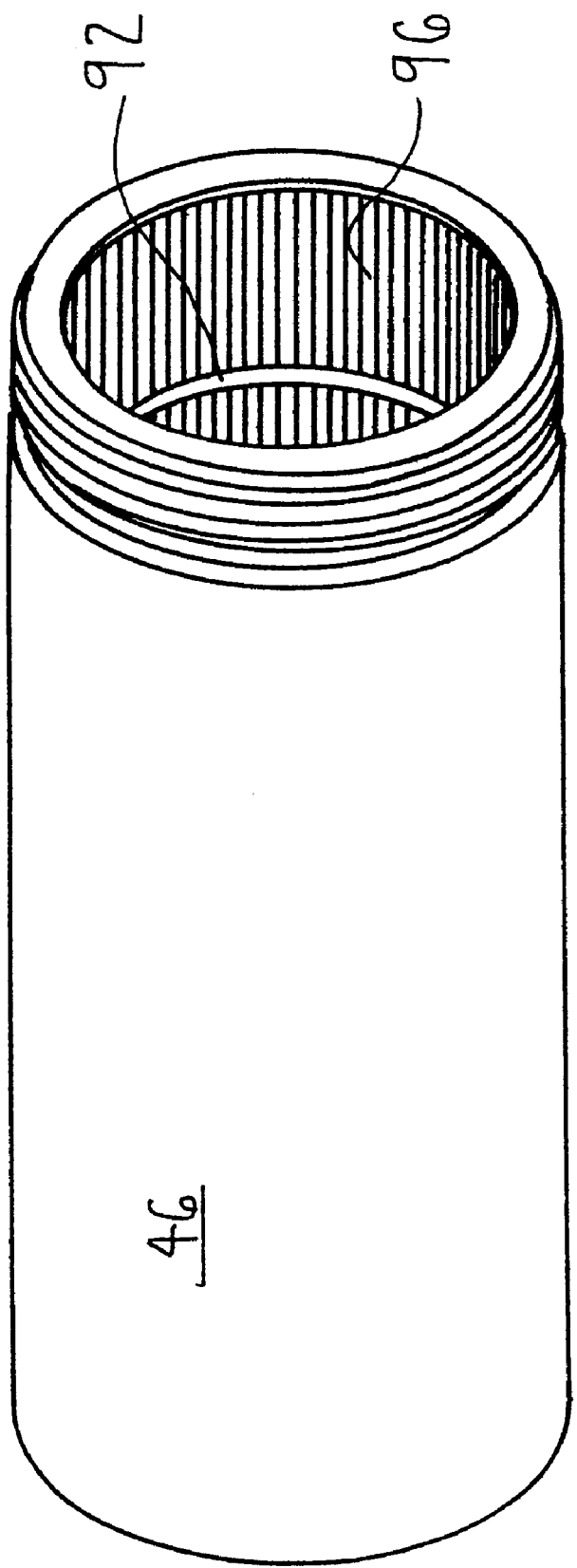
FIG. 5 is a perspective of the motor housing.

The planet gears 84 are driven by a sun gear 88. The sun gear 88 is actually the exposed end of the rotor shaft that extends out of motor housing 46. Turning more specifically to FIGS. 4 and 5, it will be seen that the rotor, as well as the other parts of the motor 26, are seated in the housing 46 so as to be spaced rearward from the front end, which is open. A circular bearing support 90 encloses the components forming the motor 26. Bearing support 90 is formed with a center hole (not identified) through which the motor rotor projects. A retaining ring 91, which is seated in a groove 92 formed in the inner wall of the motor housing 46, holds bearing support 90 in place.

The drive pin 79, extends perpendicularly through the front end of the output shaft 78. The drive pin 79 holds the inner hub of the cutting accessory 22 to the output shaft 78 so that the inner tube of the cutting accessory and the shaft rotate in unison.

The forward portion of the inner wall of the motor housing 46, the portion located forward of the retaining ring 91 to the front end of the housing, is formed to have teeth 96. These are the teeth 96 which are engaged by the planet gears 84. Thus, for the handpiece 20 of this invention, the motor housing 46 also serves as the static ring gear of the planetary gear assembly 74.

The structure of the suction valve 44 and explanation of how the valve is mounted to the handpiece is now offered by reference to FIGS. 2, 3, 7 and 8. Suction valve has a cylindrical valve body 102. A through bore 104 extends diametrically through the valve body 102. Extending coaxially away from valve body 102 is a valve stem 106. Valve stem 106 has a diameter that is less than that of the valve body 102. An L-shaped lever arm 108 is press-fit over the free end of valve stem 106. Alternatively, the lever arm 108 is formed as single piece with the valve body 102. It will be observed that the outer end of lever arm 108 is parallel with valve body 102. The lever arm 108 is shaped so that the outer end thereof extends over the top of the handpiece housing 24. It will further be noted that bottom surface of lever arm 108 is shaped to define a semi-circular groove 109. The purpose of groove 109 will be explained below.

The handpiece housing 24 is formed to define a valve bore 110, which is open at one end and closed at the other end, in which valve body 102 is seated. Valve bore 110 is located at the forward end of suction bore 42 and has a center axis that is perpendicular to the longitudinal axis of the suction bore 42. Handpiece housing 24 is further formed to define a suction passage 112 which extends diagonally forward from the front end of valve bore 110 into the main bore 40. When the suction valve 44 is in the open position, fluid is drawn out the cutting accessory 22, through the front end of the main bore 40, the suction passage 112 and the suction bore 42.

The suction valve 44 is mounted to the handpiece by seating valve body 102 in valve bore 110. Prior to this mounting, an O-ring 114 is seated over the exposed portion of the valve stem 106. The O-ring 114 provides a seal around the valve body 102.

The suction valve 44 is held in place by a pin 116 that extends through a pin bore 118 formed in front of the handpiece housing 24. More specifically the pin 116 is seated in pin bore 118 and in a groove 120 formed in the surface of the housing 24 adjacent the bottom of valve lever arm 108. When the pin 116 is seated in bore 118 and groove 120, the portion of the pin that extends above groove 120 is seated in groove 109 formed in the lever arm 108. Thus, the pin 116 locks the suction valve 44 in place.

As can be seen from FIGS. 2 and 3, the front of the handpiece housing 24 is further formed to have a reduced diameter neck 122. Pin bore 118 extends rearwardly from the stepped surface between neck 122 and the rest of the housing 24. A sleeve-like collar 124 is threadedly secured over neck 122. Collar 124 covers the open end of pin bore 118 so as to hold the pin 116 in place.

Figure 9:
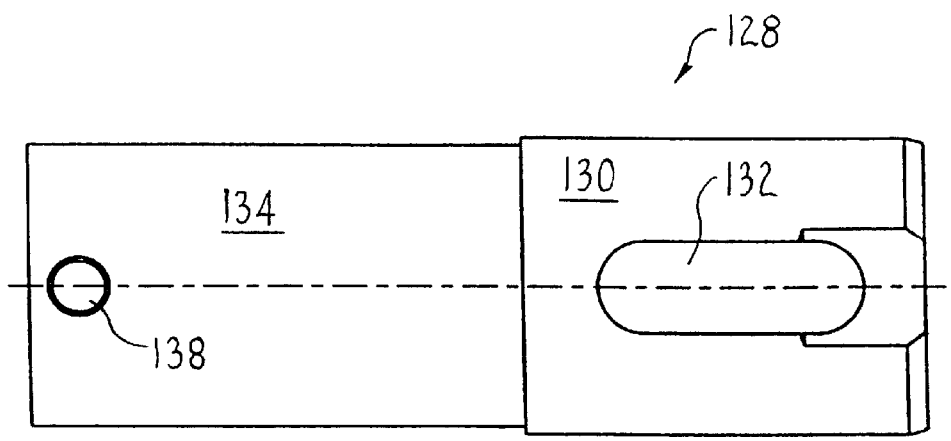
FIG. 9 is a plane view of the receptacle.
Figure 10:
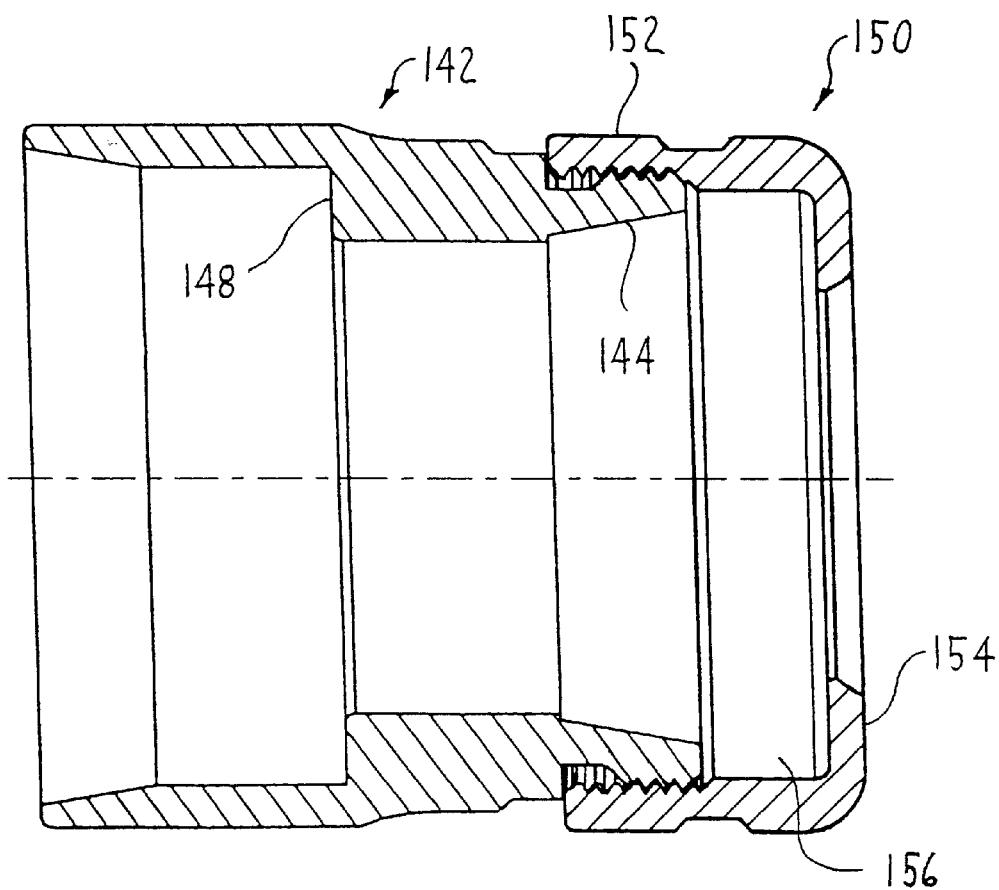
FIG. 10 is a cross sectional view of the cone sleeve and nose cap sub-assembly.

The coupling assembly 28, now described by FIGS. 2, 9 and 10, includes a sleeve like receptacle 128 that is fitted in and extends out of neck 122 of housing 24. The receptacle 128 is shaped to have a rear section 130 that is press fit in housing main bore 40. The receptacle rear section 130 is shaped to have an oval through slot 132. The oval through slot 132 provides for fluid communication from the inside of the receptacle to suction passage 112.

The receptacle 128 is further formed to have an exposed section 134 that is integrally formed with and extends forward from rear section 130. In the depicted version of the invention, the exposed section 134 of the receptacle 128 has an outer diameter less than the outer diameter of the rear section 130.

Three metal ball bearings 136 are seated in separate holes 138 formed in the forward portion of the receptacle exposed section 134. Receptacle 128 is shaped so that holes 138 have a cross-sectional profile equal to that of slice through a sphere. More particularly, the inner wall of receptacle 128 is formed so that the openings into holes 138 have a diameter less than the diameter of the ball bearings 136. Thus, the ball bearings 136 cannot pass through holes 138 into the center of the receptacle 128.

A cone sleeve 142 is fitted around the exposed end of receptacle 128 so as to surround bearings 136. The cone sleeve 142 is formed so that the inner wall thereof has a frusto-conical section 144 that tapers inwardly from the front end of the sleeve. The inside of cone sleeve 142 is further formed so as to have an annular step 148 located rearward of holes 138 that extends away from receptacle 128. The body of the cone sleeve 142, which extends rearward from the outer perimeter of step 148, projects into an annular interstitial space between inner wall of collar 124 and the outer wall of the receptacle exposed section 134.

A nose cap 150 is threadedly secured to the distal end of the cone sleeve 142. More specifically, nose cap 150 has a sleeve-like base 152. The inner wall of base 152 is provided with threading that interlocks with complementary threading formed along the outer wall of cone sleeve 142, (threading not identified). The nose cap 150 is further formed to have a lip 154 that extends inwardly towards the center axis of the handpiece 20 from the distal end of base 152. The nose cap 150 is further dimensioned so that lip 154 is positioned to be located forward of the front end of the cone sleeve 142, the forward-extending portion of the nose cap base 152 and lip 154 collectively define an annular space 156 the purpose of which will be explained below.

Coupling assembly 28 further includes a compression spring 158 that surrounds the receptacle exposed section 134. The compression spring 158 extends between the outer front surface of the housing 24 that defines main bore 40 and cone sleeve step 148. Compression spring 158 urges the cone sleeve 142 and nose cap 150 in the forward direction, towards the distal end of cutting accessory 22. The spring-induced displacement of the cone sleeve 142 forces frusto-conical section 144 towards holes 138. Thus, the frusto-conical section 144 of the cone sleeve 142 is forced against the bearings 136 to urge the bearings inwardly. This displacement of the bearings 136 holds the bearings in a complementary annular groove formed in static outer hub 30 of the cutting accessory 22 (groove not illustrated). Thus, compression spring 158, cone sleeve 142 and bearings 136 cooperate to hold the cutting accessory 22 to the handpiece 20. When the cutting accessory 22 is so coupled to the handpiece 20, the coupling assembly is referred to as being in the run state.

The coupling accessory is released from the handpiece 20 by an individual pushing the cone sleeve 142 and nose cap 152 rearwardly, towards the proximal end of the handpiece. This action results in a like translation of annular space 156 so that the space essentially surrounds the outer surface of the receptacle 128 adjacent holes 138. Once this space 156 is so defined around holes 138, when an individual pulls outwardly on the cutting accessory, the bearings 136 are forced into the space. Thus, when the coupling assembly 28 is in this state, the bearings 136 do not offer any resistance to the removal or replacement of the cutting accessory 22. When the coupling assembly 28 is in this state, it is referred to as being in the accessory load state. The coupling assembly 28 is returned to the run state by simply releasing the manual force used to force the cone sleeve 142 and nose cap 152 toward the rear end of the handpiece; spring 158 then urges the cone sleeve forward back to its run, position.

The motor 26 of this invention is designed so that its housing 46 not just houses the working components of the motor. Motor housing 46 also functions as the ring gear of the gear assembly 74 coupled to the motor. This eliminates the need to provide the handpiece 20 of this invention with a stand-alone ring gear. Thus, this invention eliminates both the expense and weight with having to provide this separate component. Moreover, still another benefit of this construction is that it eliminates the need to align a separate ring gear and the need to ensure that the separate ring gear stays in alignment.

The handpiece 20 of this invention is further constructed so that the suction valve 44 extends out of bore 110 that is only open at one side of the housing 24. This arrangement eliminates the need to have to provide seals and other components for sealing a valve bore that is constructed as a through bore. Moreover, in addition to eliminating the costs associated with providing a second seal, this invention eliminates the malfunctions and repair costs associated with a second seal.

Furthermore, the coupling assembly 28 of this handpiece 20 can be readily disassembled by unscrewing the nose cap 152 and removing the ball bearings 136. Once these components are separated from the handpiece, the cone sleeve and compression sleeve are easily removed. Thus, the coupling assembly of this invention can be easily taken apparent in order to facilitate the maintenance or repair of the handpiece.

Thus, the handpiece 20 of this invention is economical to assemble, is of reduced weight, and is easy to maintain.

It should be understood that the forgoing description has been limited to one particular version of this invention. It will be apparent that modifications can be made with the attainment of some or all of the advantages thereof. For instance, it should be recognized that not all versions of the handpiece of this invention have the described motor housing, suction valve or coupling assembly. Also, in other versions of the invention, means other than a pin may be employed to hold the suction valve 44 in position. For example, there may be times when it is desirable to employ a threaded set screw to hold the suction valve 44 in place.

Similarly, in some versions of the invention, the coupling assembly 28 may not be provided with the described ball bearings. For example, in some versions of the invention, it may be desirable to provide the coupling assembly with feet that are biased inwardly by the cone sleeve when the coupling assembly 28 is in the run state. Also, it may be desirable to provide the coupling assembly 28 with some sort of locking tab that holds the cone sleeve in the accessory load state. It may be desirable to provide this mechanism so that the medical personnel do not have to employ any mental or manual effort to hold the coupling assembly in the accessory load state while engaging in the replacement of the cutting accessories.

Therefore, it is the object of the appended claims to cover all such variations and modifications that come within the true spirit and scope of the invention.

What is claimed is:

1. A powered surgical handpiece comprising:
a handpiece housing having a bore;
a motor fitted in the housing bore, the motor having a motor housing for containing components of said motor said motor housing being statically fitted in the housing bore; a rotating motor shaft that extends out of said motor housing; and a ring gear formed as part of said motor housing that is located around said motor shaft;
a gear assembly disposed in the housing bore for transferring rotational motion of said motor shaft to a cutting accessory, said gear assembly having planet gears configured to engage said motor shaft and said ring gear and an output shaft connected to said planet gears so as to be rotated by said planet gears; and
a coupling assembly secured to said handpiece housing, said coupling assembly having at least one member that is movably attached to said handpiece housing for releasably securing the cutting accessory to said handpiece housing.

2. The powered surgical handpiece of claim 1, wherein said handpiece housing is formed with a suction bore that extends from said coupling assembly to an outlet port formed in said handpiece housing and a suction valve is seated in said handpiece housing for regulating fluid flow through said suction bore.

3. The powered surgical handpiece of claim 2, wherein: said handpiece housing is formed with a valve bore that intersects the suction bore and the valve bore is closed at one end and open at a second end; and said suction valve is seated in the valve bore and has a single stem that extends outside of said handpiece housing through the open end of the valve bore.

4. The powered surgical handpiece of claim 1, wherein said coupling assembly includes:
a center tube that is mounted to said handpiece housing, said center tube having a center opening into which the cutting accessory is inserted and a longitudinally extending center axis;
a plurality of engagement members that are movably fitted to said center tube so that said engagement members can move towards and away from the center axis of said center tube wherein when said engagement members move towards the center axis, said engagement members engage with the cutting accessory;
a cone sleeve disposed around said center tube, said cone sleeve having an inner wall with an inclined surface for urging said engagement members towards the center axis of said center tube, wherein said cone sleeve is dimensioned to move longitudinally over said center tube;
a nose cap releasably secured to said cone sleeve, said nose cap defining a space located away from said cone sleeve inner wall for receiving said engagement members when said engagement members are urged away from the center axis of said center tube; and
a spring extending between said handpiece housing and said cone sleeve for urging said cone sleeve away from said housing so that said cone sleeve inner wall is normally urged against said engagement members so that said inner wall blocks outward movement of said engagement members away from the cutting accessory.

5. A powered surgical handpiece comprising:
a handpiece housing having a bore;
a motor fitted in the housing bore, said motor having a motor housing for containing components of said motor, said motor housing being fixed relative to said handpiece housing and a rotating motor shaft that extends out of said motor housing;
a gear assembly disposed in the housing bore for transferring rotational motion of said motor shaft to a cutting accessory, said gear assembly having planet gears and a ring gear, said ring gear being formed from a section of said motor housing so as to be a single piece with said motor housing and surrounding said motor shaft, wherein said planet gears engage said motor shaft and said ring gear; and
at least one coupling element movably attached to said handpiece housing for releasably securing the cutting accessory to said handpiece housing.

6. The powered surgical handpiece of claim 5, wherein said handpiece housing is formed with a suction bore that extends from said coupling assembly to an outlet port formed in said handpiece housing and a suction valve is seated in said handpiece housing for regulating fluid flow through said suction bore.

7. A powered surgical handpiece comprising:
a housing having: a main bore; a suction bore that extends to an outlet port; and a valve bore that intersects with the suction bore, the valve bore having a closed end and an open end;

a motor fitted in the main bore;

a coupling assembly secured to said housing, said coupling assembly including at least one engagement member that is movably secured to said housing for abutting a cutting accessory to releasably hold the cutting accessory to said housing and wherein said housing is further shaped so that the suction bore extends from said coupling assembly so that the suction bore provides a fluid communication path from the cutting accessory to the outlet port;

a suction valve, said suction valve having: a valve body that is seated in the valve bore of said housing to rotate around an axis, said valve body being formed with a through bore that extends perpendicularly to the axis of rotation of said valve body; a single valve stem; that extends from said valve body through the open end of the valve bore; and a valve arm attached to said valve stem; and a retaining member removably fitted to said housing and positioned to releasably engage a portion of said valve arm to prevent removal of said suction valve from the valve bore.

8. The powered surgical handpiece of claim 7, wherein: said housing is formed with a supplemental bore separate from the main bore, the suction bore and the valve bore; and said pin is partially seated in the supplemental bore.

9. The powered surgical handpiece of claim 8, further including a collar removably attached to said housing wherein said collar is configured to close the supplemental bore to hold said pin in said supplemental bore.

10. A powered surgical handpiece, said handpiece including:

a housing, said housing having opposed ends;

a motor disposed in said housing; and a coupling assembly having at least one coupling element movably attached to said housing for engaging a cutting attachment to releasably secure said cutting attachment to said housing so that the cutting attachment rotates with actuation of said motor;

wherein, said housing has a suction assembly that extends from said coupling assembly to provide a fluid communications path from said coupling assembly, said suction assembly including:

a suction bore formed in said housing, the suction bore extending away from said coupling assembly towards an end of said handpiece;

a valve bore formed in said housing, the valve bore being positioned to intersect the suction bore, wherein said housing is formed so that the valve bore has a closed end and an open end opposite the closed end;

a valve, said valve having: a valve body that is rotatably seated in the valve bore, said valve body having a through hole; a single stem that extends from said valve body through the open end of the valve bore; and a lever attached to said stem for setting an open/closed state of said valve; and a pin removably mounted to said housing for abutting said valve to releasably secure said valve in the valve bore.

11. The powered surgical handpiece of claim 10, wherein: said pin is seated in a supplemental bore formed in said housing; and a member is releasably secured to said housing over said supplemental bore to hold said pin in said supplemental bore.

12. The powered surgical handpiece of claim 10, wherein said valve has a lever arm that extends from said stem and said lever arm has a free end that extends across said housing.

13. A powered surgical handpiece for receiving a cutting accessory through which a suction is drawn, said handpiece including:

a housing, said housing having first and second ends, and a suction bore that extends from the first end towards the second end;

a motor disposed in said housing; and a coupling assembly having:

a receptacle extending from the first end of said housing, said receptacle having a center axis and an open end for receiving the cutting accessory;

a plurality of engagement members movably fitted to said receptacle so that said engagement members can move towards and away from the center axis of said receptacle, wherein, when said engagement members move towards the center axis, said engagement members engage with the cutting accessory;

a cone sleeve disposed around said receptacle, said cone sleeve having an inner wall with a surface for urging said engagement members towards the center axis of said receptacle and an outer wall on which at least one locking member is formed, wherein said cone sleeve is dimensioned to move longitudinally over said receptacle;

a nose cap disposed over said cone sleeve, said nose cap having an inner wall on which at least one locking member is formed wherein said nose cap locking member releaseably engages said cone sleeve locking member so that said locking members removably hold said nose cap to said cone sleeve and said nose cap defines a space located away from said cone sleeve inner wall for receiving said engagement members when said engagement members are urged away from the center axis of said receptacle; and a spring extending between said housing and said cone sleeve for urging said cone sleeve away from said housing so that said cone sleeve inner wall is normally urged against said engagement members so that said inner wall blocks outward movement of said engagement members away from the cutting accessory, wherein said housing is further formed so that the suction bore extends to said receptacle and said receptacle is formed with an opening that provides fluid communication from inside said receptacle to the suction bore.

14. The powered surgical handpiece of claim 13, wherein said engagement members are rotatably fitted to said receptacle.

15. The powered surgical handpiece of claim 13, wherein said inner wall of said cone sleeve has a inclined profile.

16. The powered surgical handpiece of claim 13, wherein said nose cap is threadedly secured to said cone sleeve.

17. The powered surgical handpiece of claim 16, wherein said engagement members are ball bearings and the inner wall of said cone sleeve has an inclined profile.

18. The powered surgical handpiece of claim 13, wherein a valve is mounted to said housing for regulating fluid flow through the suction bore.

19. The powered surgical handpiece of claim 17, wherein:

said valve includes a valve body that is removably fitted in a closed-end bore formed in said housing and a pin that is seated in a supplemental bore formed in said housing, said pin being positioned to abut said valve body and the supplemental bore has an opening in said housing adjacent said receptacle; and a collar is removably secured to said housing so as to be located around said receptacle and is positioned to cover the opening of the supplemental bore to hold said pin in the supplemental bore.

20. The powered surgical handpiece of claim 5, wherein said at least one coupling element is a ball bearing.

21. The powered surgical handpiece of claim 7, wherein said at least one engagement member is a ball bearing.

22. The powered surgical handpiece of claim 10, wherein said at least one coupling element is a ball bearing.

23. The powered surgical tool of claim 10, wherein a valve arm is attached to said valve stem and said pin is positioned to abut portion of said valve arm.

24. A powered surgical handpiece for receiving a cutting accessory through which a suction is drawn, said handpiece including:

a housing, said housing having a front end and a suction bore that extends rearwardly from the front end;

a motor disposed in the housing, said motor having an output shaft for engaging a complementary portion of the cutting accessory;

an inner sleeve mounted to the front end of said housing, said inner sleeve defining a center space and an open front end for receiving the cutting accessory and a center axis and wherein the suction bore of said housing extends from the center space;

a plurality of engagement members movably attached to said inner sleeve wherein, said engagement members are selectively movable towards and away from the center axis of the center opening of said inner sleeve;

an outer sleeve disposed around said inner sleeve and capable of longitudinal movement over said inner sleeve, said outer sleeve having an inner wall dimensioned to abut said engagement members to urge said engagement members towards the center axis of said inner sleeve and at least one locking member is formed on a front portion of said outer sleeve, said outer sleeve having a first position relative to said inner sleeve in which the inner wall abuts said engagement members and a second position in which the inner wall is spaced from said engagement members;

a nose cone disposed over a front end of said outer sleeve said nose cone having at least one locking member wherein said nose cone locking member is positioned to releaseably engage said outer sleeve locking member so that said locking members removably hold said nose cone to said outer sleeve and, said nose cone defining a space located forward of the inner wall of said outer sleeve for receiving the engagement members when said outer sleeve is in the second position; and a spring extending between said housing and said outer sleeve for releasably holding said outer sleeve in the first position.

25. The powered surgical handpiece of claim 24, wherein said engagement members are rotatably fitted to said inner sleeve.

26. The powered surgical handpiece of claim 24, wherein the inner wall of said outer sleeve has an inclined profile.

27. The powered surgical handpiece of claim 24, further including a valve mounted to said housing for regulating fluid flow through the suction bore.

28. The powered surgical handpiece of claim 27, wherein said valve includes a valve body that is rotatingly fitted in said housing.

29. The powered surgical handpiece of claim 24, wherein said inner sleeve is relesably secured to said housing and a collar is removably secured to the front end of said housing, said collar being dimensioned to engage said inner sleeve to hold said inner sleeve to said housing.

* * * * *

UNITED STATES PATENT AND TRADEMARK OFFICE
CERTIFICATE OF CORRECTION

PATENT NO.     : 6,312,441 B1
DATED          : November 6, 2001
INVENTOR(S)    : Wenjie Deng It is certified that error appears in the above-identified patent and that said Letters Patent is hereby corrected as shown below:

Column 7,
Line 48, change "having a" to -- having: a --
Line 50, change "motor said" to -- motor, said --

Column 8,
Line 20, change "tube wherein when" to -- tube wherein, when --

Column 9,
Line 15, change "valve stem; that" to -- valve stem that --
Line 25, change "said pin is partially" to -- said retaining member is a pin partially --

Column 10,
Line 59, change "of Claim 17" to -- of Claim 18 --

Signed and Sealed this

Seventeenth Day of September, 2002

*Attest:*

*Attesting Officer*

JAMES E. ROGAN
*Director of the United States Patent and Trademark Office*